United States Patent [19]

Unuma et al.

[11] 4,338,461

[45] Jul. 6, 1982

[54] PROCESS FOR PRODUCING D-2-AMINO-2-(1,4-CYCLOHEXADIENYL)ACETIC ACID

[75] Inventors: Kunio Unuma; Hiroyasu Saito; Jihei Inomata, all of Iwaki; Saburo Takizawa, Morioka, all of Japan

[73] Assignee: Nippon Kasei Chemical Co., Ltd., Fukushima, Japan

[21] Appl. No.: 245,437

[22] Filed: Mar. 19, 1981

[30] Foreign Application Priority Data

Apr. 21, 1980 [JP] Japan ................................. 55-52590

[51] Int. Cl.$^3$ ............................................. C07C 99/00
[52] U.S. Cl. ................................................... 562/507
[58] Field of Search ........................................ 562/507

[56] References Cited

U.S. PATENT DOCUMENTS 2,182,242 12/1939 Wooster et al. .................... 260/667
3,485,819 12/1969 Welsenborn ...................... 260/239.1
3,682,981 8/1972 Welsenborn et al. ............... 260/396

FOREIGN PATENT DOCUMENTS 1445767 5/1966 France.
419123 4/1976 Spain .................................. 562/507

OTHER PUBLICATIONS

House, Modern Synthetic Reactions, pp. 145–146, 190, 494 (1972).
Carruthers, Some Modern Methods of Organic Synthesis, pp. 432–433, 443–444, 449, 452, (1975).

*Primary Examiner*—Robert Gerstl
*Attorney, Agent, or Firm*—Wegner & Bretschneider

[57] ABSTRACT

A novel process for producing D-2-amino-2-(1,4-cyclohexadienyl)-acetic acid useful as an intermediate compound for producing 6-aminopenicillanic acid or 7-aminocephalosporanic acid is disclosed.

2 Claims, No Drawings

4,338,461

PROCESS FOR PRODUCING D-2-AMINO-2-(1,4-CYCLOHEXADIENYL)ACETIC ACID

SUMMARY OF THE INVENTION

The present invention relates to a novel process for producing D-2-amino-2-(1,4-cyclohexadienyl)acetic acid which has been used as an intermediate compound for producing 6-aminopenicillanic acid or 7-aminocephalosporanic acid is prepared by reducing D-2-aminophenyl-acetic acid with metallic sodium in a mixed solvent of liquid ammonia and water.

BACKGROUND OF THE INVENTION

Hitherto, as a process for producing D-2-amino-2-(1,4-cyclohexadienyl)acetic acid, a process for reducing D-2-aminophenyl-acetic acid with metallic lithium and t-butyl alcohol in liquid ammonia (U.S. Pat. No. 3,682,981) and a process for reducing D-2-aminophenylacetic acid with metallic sodium and an alcohol in liquid ammonia (Spanish Pat. No. 419,123) have been known.

However, since in the process disclosed in U.S. Pat. No. 3,682,981, it is necessary to use an expensive metallic lithium, the process is economically unprofitable, and on the other hand, there is a demerit in the process disclosed in Spanish Patent 419,123 that the rate of reduction of D-2-aminophenylacetic acid is low.

Moreover, since in these publicly known processes an alcohol is used as a proton donor for the reaction of reduction, the alcohol must be recovered industrially after the reaction is over, and the following procedures are adopted for the recovery of alcohol:

After decomposing alcoholate of metallic lithium or metallic sodium, which has formed in the reaction system, by triethylamine hydrochloride, ammonia in the reaction system is evaporated off, and the unreacted D-2-aminophenylacetic acid and the reaction product, D-2-amino-2-(1,4-cyclohexadienyl)acetic acid, which remain in the system as a mixture with the alcohol in a state of slurry are heated to evaporate the alcohol to be recovered.

However, such a method of recovering the alcohol by evaporation might lead D-2-aminophenylacetic acid and D-2-amino-2-(1,4-cyclohexadienyl)acetic acid remaining in the above-mentioned mixture into racemization. For preventing such racemization, it is necessary to evaporate the alcohol in the mixture under a reduced pressure at a relatively low temperature to be recovered, and in such a case of evaporation of alcohol under a reduced pressure, D-2-aminophenylacetic acid and D-2-amino-2-(1,4-cyclohexadienyl)acetic acid in the mixture are entrained as a solid matter with the evaporating alcohol, and accordingly, the effective recovery of the alcohol is difficult.

In consideration of the demerits of the publicly known processes which use an alcohol in the production of D-2-amino-2-(1,4-cyclohexadienyl)acetic acid, the present inventors have studied processes for effectively producing D-2-amino-2-(1,4-cyclohexadienyl)acetic acid from D-2-aminophenylacetic acid, and have attained the present invention.

DETAILED DESCRIPTION OF THE INVENTION

The object of the present invention is to offer a process for effectively producing D-2-amino-2-(1,4-cyclohexadienyl)acetic acid from D-2-aminophenylacetic acid without using any alcohol. The other object of the present invention will be made clear from the following descriptions:

The characteristic feature of the process according to the present invention is to produce D-2-amino-2-(1,4-cyclohexadienyl)acetic acid by reducing the starting material, D-2-aminophenylacetic acid, with metallic sodium in a medium of a mixture of liquid ammonia and water.

The ratio of liquid ammonia to water in a mixture thereof which is used as a reaction medium in the process according to the present invention may be varied in a broad range, however, it is preferably from 50:50 to 93:7 by weight, and particularly, for the easy removal of the unreacted substance from the reaction system, the weight ratio of liquid ammonia to water is still preferably from 65:35 to 82:18.

In the case where water is solely used as the reaction medium, there is a danger of causing explosion during the reaction, and accordingly, the reaction is not be carried out safely.

The amount of the reaction medium of a mixture of liquid ammonia and water for use in the process is, preferably 3 to 5.5 kg per mole of the starting material, D-2-aminophenylacetic acid, and the less amount leads to the reducing rate of reduction in the process and on the other hand, the larger amount not only leads to the restriction of the feed amount of the starting material but also to the longer period for recovering liquid ammonia after the reaction is over, and thus both cases are not favorable.

Metallic sodium used in the present invention reacts with water in the reaction medium to generate hydrogen which contributes to the reduction of D-2-aminophenylacetic acid while transforming into sodium hydroxide which reacts with the thus formed D-2-amino-2-(1,4-cyclohexadienyl)acetic acid and the unreacted D-2-aminophenylacetic acid to convert them into their sodium salts, respectively. Accordingly, in the case where metallic sodium is used in an amount of more than the equimolar amount to the starting material, D-2-aminophenylacetic acid, the unreacted acid or the reaction product, D-2-amino-2-(1,4-cyclohexadienyl)acetic acid is obtained as the respective sodium salts thereof dissolved in water after the reaction is over. Therefore, by adding an acidic substance such as sulfuric and hydrochloric acid into the solution of the salts, D-2-aminopheylacetic acid or D-2-amino-2-(1,4-cyclohexadienyl)acetic acid is separated out from the aqueous solution to be easily recovered.

In consideration of the foregoing, it is preferable to use metallic sodium in an amount of more than the equimolar amount to the starting material, more preferably in a range of 3 to 10 mole per mole of D-2-aminophenylacetic acid.

In the next place, although it is necessary to maintain the reaction temperature of the process of the present invention sufficiently low so as to prevent the racemization of the optically active D-2-aminophenylacetic acid and the optically active D-2-amino-2-(1,4-cyclohexadienyl)acetic acid, on the other hand, in the case where the reaction temperature is too low, the rate of dissolution of metallic sodium into the reaction medium is reduced to cause the longer time period of the reaction. Accordingly, in practice, the reaction temperature should be maintained at lower than −20° C., preferably in a range of −50° to −25° C.

The reaction is completed within about 30 minutes at the above-mentioned temperature. The completion of reaction can be confirmed by the complete consumption of metallic sodium introduced into the reaction system.

In the practice of the present invention, D-2-aminophenylacetic acid as the starting material and water are introduced into a reaction vessel, and then liquid ammonia is added to the system so as to make the weight ratio of liquid ammonia to water to be in the afore-mentioned range under agitation while maintaining the temperature of the system in the afore-mentioned range to dissolve the starting material into the reaction medium, and an amount of metallic sodium more than the equimolar amount of D-2-aminophenylacetic acid. Upon dissolving metallic sodium into the system containing the reactants, the reaction mixture once colours to blue and bubbles of gaseous hydrogen generate, and as the reaction proceeds, the colour of the reaction mixture changes from blue to white. The complete change of colour to white shows the completion of the reaction.

After the reaction is over, the temperature within the vessel is gradually raised to evaporate liquid ammonia to be recovered, and the remaining reaction mixture is filtered to remove the water-insoluble matter and to obtain a clear aqueous solution as the filtrate. On adjusting the pH of the aqueous solution by adding an acidic substance such as sulfuric or hydrochloric acid, raw product of D-2-amino-2-(1,4-cyclohexadienyl)acetic acid is possibly obtained as white crystals.

As has been described, by controlling the weight ratio of liquid ammonia to water in the mixed reaction medium, the weight ratio of the reaction medium to the starting material and the reaction temperature, D-2-amino-2-(1,4-cyclohexadienyl)acetic acid is effectively produced from D-2-aminophenylacetic acid without using any alcohol, and such a fact is really surprising.

Because, in the publicly known process disclosed in U.S. Pat. No. 3,682,981 and Spanish Pat. No. 419,123, it has been considered that the presence of water in the reaction medium impedes the reduction of D-2-aminophenylacetic acid, and accordingly, it has been supposed that the use of a reaction medium of moisture-free liquid ammonia and an absolutely dried alcohol is necessary. In consideration of such a recognition, it could not have been presumed from the state of art that water acts effectively as a reaction medium in the co-presence of liquid ammonia.

Also in consideration of that in the case of reducing the aromatic ring of a compound having the aromatic ring by an alkali metal in liquid ammonia, it has been known that the aromatic ring is reduced into dihydrogenated- and tetrahydrogenated rings, it could not have been presumed from the state of art that D-2-aminophenylacetic acid is selectively reduced only to the dihydrogenated compound, i.e., D-2-amino-2-(1,4-cyclohexadienyl)acetic acid, according to the present invention.

The present invention will be exemplified by non-limitative examples as follows:

EXAMPLE 1

In a 5-liter round-bottomed glass flask provided with a stirrer, a thermometer, an inlet for metallic sodium and an outlet for evaporating gaseous ammonia and generating gaseous hydrogen to ambient atmosphere, 100 g (0.66 mol) of D-2-aminophenylacetic acid showing a specific rotatory power of $[\alpha]_D^{25} = -110°$ and 140 g of water were cooled to −35° C.

Into the cooled mixture, 1860 g of liquid ammonia was added and the content of the flask was stirred to dissolve D-2-aminophenylacetic acid. Then 92 g (3.91 mols) of small pieces of metallic sodium were added while controlling its rate of addition so as not to raise the temperature of the reaction mixture to higher than −25° C. during 30 min. Meanwhile, metallic sodium gradually dissolved into the reaction mixture with the colouring of reaction mixture to blue and the incessant evolution of gaseous hydrogen.

After 10 min of the completion of addition of metallic sodium, it was confirmed that the colour of reaction mixture changed from blue to white and metallic sodium has been completely consumed, and then the temperature of reaction mixture was gradually raised to evaporate liquid ammonia off, and the thus obtained sludge of reaction mixture was subjected to filtration to collect a clear aqueous solution.

While cooling the aqueous solution, 35% hydrochloric acid was added to the solution of bring its pH to 6.5, and the thus precipitated white crystals were collected by filtration.

After washing the thus obtained crystals three times with de-ionized water, they were dried under a reduced pressure. By analyzing the thus obtained product with nuclear magnetic resonance spectroscopy following the method described in J. Pharmaceut. Sci., Vol. 65(5), pages 738–740 (1976) and determining its specific rotatory power, in 2N NaOH aq. at 1% in concentration it was confirmed that the product was raw D-2-amino-2-(1,4-cyclohexadienyl)acetic acid still containing the starting material, D-2-aminophenylacetic acid.

The thus obtained values of its specific rotatory power, its weight (including the starting material) and its yield are shown in Table 1 with those values of the products in Examples 2 to 10.

The above-mentioned value of its yield was obtained by a gas chromatographic analysis of the product after subjecting the above-mentioned raw product to trimethylsilylization with bis-(trimethylsilyl)trifluoroacetamide.

EXAMPLES 2 to 10

In the same manner as in Example 1 except for changing the amount of liquid ammonia and water for use in the reduction as shown in Table 1, raw product of D-2-amino-2-(1,4-cyclohexadienyl)acetic acid was produced. The values of its specific rotatory power, its weight containing the starting material and its yield obtained as in Example 1 are shown also in Table 1.

TABLE 1

| No. of example | Amount of reaction medium (g) | | Specific rotatory power $[\alpha]_D^{26}$ (°) | Weight of product (g) | Yield (%)** |
|---|---|---|---|---|---|
| | liq.NH$_3$* | water | | | |
| 1 | 1860 | 140 | −116 | 94.1 | 8.6 |
| 2 | 1740 | 260 | −115 | 93.9 | 35.3 |
| 3 | 1640 | 360 | −115 | 93.5 | 68.0 |
| 4 | 1540 | 460 | −120 | 93.0 | 83.3 |
| 5 | 1460 | 540 | −118 | 92.6 | 84.7 |
| 6 | 1420 | 580 | −115 | 92.5 | 82.5 |
| 7 | 1320 | 680 | −117 | 92.2 | 66.0 |
| 8 | 1260 | 740 | −116 | 91.8 | 46.7 |
| 9 | 2500 | 1000 | −118 | 90.5 | 95.1 |

TABLE 1-continued

| No. of example | Amount of reaction medium (g) | | Specific rotatory power $[\alpha]_D^{26}$ (°) | Weight of product (g) | Yield (%)** |
|---|---|---|---|---|---|
| | liq.NH$_3$* | water | | | |
| 10 | 2660 | 840 | −116 | 91.0 | 96.9 |

Note:
*liquid ammonia.
**vs. theoretical value.

What is claimed is:

1. A process for producing D-2-amino-(1,4-cyclohexadienyl) acetic acid, comprising the steps of reducing D-2-aminophenylacetic acid with metallic sodium in the presence of a mixture of liquid ammonia and water and adding an acidic substance to the resultant aqueous solution, the weight ratio of liquid ammonia to water in said mixture being in the range of 65:35 to 82:18.

2. A process according to claim 1, wherein said reduction is carried out at a temperature of from −25° C. to −50° C.